United States Patent
Hamas et al.

(10) Patent No.: US 8,556,968 B2
(45) Date of Patent: Oct. 15, 2013

(54) BREAST IMPLANT WITH LOW COEFFICIENT OF FRICTION BETWEEN INTERNAL SHELLS IN AN AQUEOUS FLUID ENVIRONMENT

(75) Inventors: Robert S. Hamas, Dallas, TX (US);
Dwight D. Back, Irving, TX (US);
Kevin Yacoub, Los Olivos, CA (US)

(73) Assignee: Ideal Implant Incorporated, Dallas, TX (US)

( * ) Notice: Subject to any disclaimer, the term of this patent is extended or adjusted under 35 U.S.C. 154(b) by 0 days.

(21) Appl. No.: 13/292,303

(22) Filed: Nov. 9, 2011

(65) Prior Publication Data

US 2013/0116784 A1    May 9, 2013

(51) Int. Cl.
*A61F 2/12*    (2006.01)

(52) U.S. Cl.
USPC .............................................................. 623/8

(58) Field of Classification Search
USPC .......................................................... 623/7–8
See application file for complete search history.

(56) References Cited

U.S. PATENT DOCUMENTS

| | | | |
|---|---|---|---|
| 4,264,990 A * | 5/1981 | Hamas | 623/8 |
| 4,298,998 A * | 11/1981 | Naficy | 623/8 |
| 4,531,244 A | 7/1985 | Hamas | |
| 4,731,081 A | 3/1988 | Tiffany et al. | |
| 4,773,909 A * | 9/1988 | Chaglassian | 623/8 |
| 4,955,907 A * | 9/1990 | Ledergerber | 623/8 |
| 4,960,425 A | 10/1990 | Yan et al. | |
| 5,358,521 A * | 10/1994 | Shane | 623/8 |
| 5,496,367 A | 3/1996 | Fisher | |
| 5,653,755 A * | 8/1997 | Ledergerber | 623/8 |
| 5,736,251 A | 4/1998 | Pinchuk | |
| 5,779,734 A * | 7/1998 | Ledergerber | 623/8 |
| 6,113,634 A * | 9/2000 | Weber-Unger et al. | 623/7 |
| 6,146,418 A * | 11/2000 | Berman | 623/8 |
| 6,802,861 B1 * | 10/2004 | Hamas | 623/7 |
| 7,615,074 B2 * | 11/2009 | Carvalio | 623/8 |
| 7,645,475 B2 | 1/2010 | Prewett | |
| 2002/0038147 A1 * | 3/2002 | Miller, III | 623/8 |
| 2008/0221678 A1 * | 9/2008 | Hamas | 623/8 |
| 2008/0221679 A1 | 9/2008 | Hamas | |
| 2009/0299472 A1 * | 12/2009 | Huang | 623/7 |
| 2010/0137985 A1 * | 6/2010 | Purkait | 623/8 |
| 2011/0270392 A1 * | 11/2011 | Schuessler et al. | 623/8 |
| 2011/0276133 A1 * | 11/2011 | Liu et al. | 623/8 |
| 2011/0288639 A1 * | 11/2011 | Trilokekar et al. | 623/8 |
| 2013/0116784 A1 * | 5/2013 | Hamas et al. | 623/8 |

* cited by examiner

*Primary Examiner* — Suzette J Gherbi
(74) *Attorney, Agent, or Firm* — The Webb Law Firm

(57) ABSTRACT

A fluid-filled surgically-implantable prosthetic device encloses one or more non-enclosing fitted shells arranged adjacent to and in a graduated relation to each other. The invention relates specifically to implantable breast prostheses with a low coefficient of friction between two or more interacting elastomeric shells in an aqueous fluid environment, without the addition of a lubricating agent to the fluid.

14 Claims, 2 Drawing Sheets

BREAST IMPLANT WITH LOW COEFFICIENT OF FRICTION BETWEEN INTERNAL SHELLS IN AN AQUEOUS FLUID ENVIRONMENT

BACKGROUND OF THE INVENTION

1. Field of the Invention

This invention relates generally to surgically-implantable prosthetic devices and, more specifically, to breast prostheses. The invention relates specifically to implantable breast prostheses with a low coefficient of friction between two or more interacting elastomeric shells in an aqueous fluid environment, without the addition of a lubricating agent to the fluid.

2. Description of Related Art

It has become a practice in the field of surgery to place a prosthetic implant in various areas of the body under any one of various conditions. In cases where cancerous, precancerous, or other abnormal or damaged tissue has been removed, the prosthetic implant is often used as a replacement for the removed tissue. Its purpose is to restore the original body contour. An implant of this character provides physical support for the surrounding body tissue. By filling any voids that are created by the removal of the body tissue, it preserves the normal outward appearance and feel of the body. Prosthetic devices have also been used to enhance or augment the appearance of body parts.

Breast prostheses have long been used for breast augmentation and for reconstructive surgery following a mastectomy. The prostheses are available in numerous sizes and shapes including teardrop, round, low profile, and high profile. Usually, breast prostheses are implanted via a small inframammary or peri-aerolar incision into a pocket dissected deep to the patient's own breast tissue in front of the pectoral muscle. In certain situations, the prosthesis may be placed behind the various chest muscles.

Some prosthetic devices have utilized a single shell or envelope, which is filled with a silicone gel, a saline solution, or other liquid, such as an oil or polymer. Other breast prosthetic devices have contained a combination of silicone gel and saline solution in separate compartments or lumens. Prior art silicone gel devices have tactile properties similar to normal tissue, but suffer from certain disadvantages. First, some silicone may bleed through the envelope and migrate out of the implant into the tissue, or into an adjacent saline filled compartment of the implant. Second, rupture of the envelope of a silicone gel implant is difficult for a patient to detect, and may require a Magnetic Resonance Imaging (MRI) scan for diagnosis.

Some breast prosthetic devices have utilized a single shell or envelope, which is filled with a saline solution. The prior art saline solution filled prosthetic devices suffer from certain disadvantages and lack the proper appearance and tactile properties due to several factors. First, the saline solution displaces too quickly to give the proper tactile properties. Second, the ease of displacement of the saline solution can create a "fluid wave" in the implant presenting an unnatural look of the prosthetic device. Third, when the saline solution displaces from one area of the implant, the lack of volume in that area may result in visible wrinkling of the shell. Fourth, the outer shell can fold upon itself, causing an area of wear (e.g., fold-flaw), leading to failure and deflation.

There are also breast prosthetic devices utilizing a single shell or envelope wherein the envelope contains baffle-forming material. The baffle-forming material fills at least a portion of the envelope, while the remainder of the envelope is filled with a fluid, such as saline solution. The baffle-forming material may or may not be attached to the envelope. The drawback to such prior art baffle-forming material is that such material may not match the single layer structure, geometry, proportions, etc., of the envelope, thereby resulting in wrinkling and folding of the implant due to the uncontrolled position of the baffle-forming material. Additionally, some of the prior art baffle material can bunch up in a portion of the implant and be felt through the shell, resulting in an unnatural feel to the implant. As described in U.S. Pat. No. 6,802,861, the position of the baffle-forming material within a breast implant can be controlled by a structure consisting of an inner shell defining a fluid-containing inner lumen surrounded by an outer shell defining a fluid-containing outer lumen and with one or more non-enclosing fitted shells in the outer lumen comprising the baffle-forming material. This arrangement of lumens, non-enclosing fitted shells, inner shell and outer shell decreases the displacement rate of the fluid, thereby improving the tactile characteristics and reducing the "fluid wave" effect compared to prior art single shell, saline filled devices. Furthermore, this non-enclosing fitted shell arrangement prevents wrinkling, folding or bunching together of the baffle material within the implant. Additionally, the outer shell is supported, feels smooth externally, and does not fold upon itself to create wear points. U.S. Pat. No. 6,802,861 teaches that a saline solution would be an appropriate choice for use as the fluid, however, other fluids may be utilized such as organic polymers or protein fluids. In addition, U.S. Pat. No. 6,802,861 teaches that lubricating agents may be added to the saline. While organic polymers, protein fluids and added lubricating agents may provide a consistent lubricating layer between the various interacting shells within the implant, in the event of rupture, they may cause an undesirable tissue response. Saline solution is the most desirable fluid to utilize to fill the implant, because in the event of rupture, saline does not cause a tissue response and is safely absorbed into the body tissue. However, saline may not provide a consistent lubricating layer between the various interacting shells within the implant, which may allow the shells in some areas of the implant to intermittently stick together and give the implant an undesirable tactile feel.

Typically, the shells of implantable breast prostheses are formed from solvent dispersions of high temperature vulcanizing (HTV) or room temperature vulcanizing (RTV) silicone. Aqueous fluids, such as saline solution, do not appreciably wet the surface of silicone, and are inviscid. Furthermore, a thin fluid film between two silicone surfaces can be easily displaced from an area, for example, when the shell surfaces are compressed together, as may occur when a breast implant with two or more shells is manipulated or palpated with fingertips. Displacement of the aqueous fluid from an area between the shells removes the aqueous fluid that was providing a consistent lubricating layer in that area, allowing the two silicone surfaces in that area to interact and "stick" as described above.

Silicone surfaces may stick together because they can have high coefficients of friction (static or kinetic), making it difficult for one silicone surface to slide while in contact with another silicone surface (ASTM standard D1894 is one means to measure the coefficients of friction of plastic film and sheeting). "Stiction," a contraction of static friction, is also a term sometimes used to describe the interaction of such surfaces and their tendency to form cohesive or adhesive bonds, which cause them to stick together. This type of bonding can have a chemical basis (e.g., hydrogen bonding, Van der Waals forces, or electrostatic forces), or a mechanical basis (e.g., interlocking asperities), or a combination of both.

Various surface chemical modifications, applied coatings, lubricating fluids such as organic polymers and addition of lubricants to aqueous fluids such as saline have been proposed to lower the coefficient of friction and improve how two elastomeric surfaces interact and slide across each other ("slidability"), thereby reducing sticking and abrasion of the surfaces. See, for example, U.S. Pat. No. 5,736,251. Chemical modifications of the surface (e.g., plasma) and application of coatings to the surface can alter the surface of the silicone, changing how two surfaces interact. Lubricating fluids such as organic polymers and the addition of lubricants to aqueous fluids such as saline provide a physical layer separating the two silicone surfaces so that the surfaces do not directly interact and stick. U.S. Patent No. 4,731,081 describes the addition of a lubricant to the saline solution in a breast implant to increase slidability of the interior surfaces of the shell when folded upon itself.

Rather than the direct addition of a lubricant to the fluid in a lumen to separate the surfaces between interacting silicone shells of a breast implant, a lubricant can be indirectly added to the fluid in a lumen by diffusion through the shell from an adjacent silicone gel filled lumen. For example, dual shell/dual lumen breast implants have been marketed that are a combination of silicone gel filled and saline filled lumen. Considering an implant that has a silicone gel filled inner lumen and saline filled outer lumen, lubricating chemical species can diffuse through the inner lumen shell into the outer lumen, providing a layer of lubricity if contacted by the interior surface of the outer shell and/or the exterior surface of the inner shell. As an additional example, a dual shell/dual lumen implant with a silicone gel filled outer lumen and saline filled inner lumen can have lubricating chemical species diffuse through the inner lumen shell into the inner lumen, providing a layer of lubricity if contacted by the interior surface of the inner shell.

It is an object of the present invention to provide a surgically-implantable prosthetic device filled with only saline and/or other aqueous fluids and which has the appropriate tactile feel, appearance, and other characteristics found in a human breast. The present invention provides a low coefficient of friction and high slidability between two or more interacting elastomeric shells in an aqueous fluid environment without the addition of a lubricating agent to the fluid, thereby providing the implant with a natural tactile feel that is similar to human breast tissue.

Another object of this invention is to provide a low coefficient of friction (e.g., static and/or kinetic coefficient of friction) and high slidability between two or more interacting silicone shells in an aqueous fluid environment within a prosthetic device with two or more shells, by applying a surface texture on at least one of the two shells that interact to maintain a sufficient amount or volume of fluid in reservoirs at surfaces to provide a consistent lubricating layer between the two interacting shells.

Yet another object of this invention is to provide a consistent lubricating layer of aqueous fluid between two or more interacting shells within an implant with two or more shells, to reduce or prevent intermittent sticking together of the shells in one or more areas, thereby giving the implant a more desirable and natural tactile feel.

SUMMARY OF THE INVENTION

Briefly, according to the present invention, there is provided a surgically-implantable prosthetic device, comprising an outer enclosing shell having an exterior surface, an interior surface, and enclosing an outer lumen or compartment, wherein the outer lumen is able to accommodate a first fluid therein. The prosthetic device further comprises an inner enclosing shell having an exterior surface, an interior surface, and enclosing an inner lumen or compartment, wherein the inner lumen is able to accommodate a second fluid therein. Additionally, the prosthetic device has one or more non-enclosing fitted shells situated between the exterior surface of the inner shell and the interior surface of the outer shell. The non-enclosing fitted shells are adjacent to each other such that all surfaces of the non-enclosing fitted shells are in communication with the outer fluid.

Both the outer shell and the inner shell are at least partially filled with an aqueous fluid. The fluid is able to move within the outer lumen and envelop the non-enclosing fitted shells. A saline solution would be an appropriate choice for use as the fluid. Saline refers to any electrolyte combination together with water; however, the invention is not limited solely to the use of saline. Other fluids that are substantially aqueous may also be utilized. For example, multiple-shelled implants filled with aqueous solutions that contain non-lubricating water-soluble species including, but not limited to, surfactants, antibiotics, and polymers are contemplated, and will also benefit from this invention.

The prosthetic device utilizing saline or the like provides a safe and harmless prosthetic implant. If the outer shell is ruptured or compromised in any fashion, the saline is safely absorbed into the body tissue. Furthermore, the patient would observe the decrease in volume of the implant and make the diagnosis of shell rupture, without the need for diagnostic tests such as a Magnetic Resonance Imaging (MRI) scan.

The outer lumen and/or the inner lumen may be pre-filled prior to implantation or, alternatively, may be first implanted and then filled with the fluid. One or more valves may be provided for the filling of the outer lumen, which includes the spaces between the non-enclosing fitted shells, and for filling of the inner lumen.

The arrangement of the lumens, the non-enclosing fitted shells, and the inner and outer shells decreases the displacement rate of the fluid. This restriction of the ability of the fluid to move inside the outer lumen improves the tactile characteristics of the implant compared to single-lumen prior art implants filled with an aqueous fluid and reduces the "fluid wave" effect of the fluid within the implant. Furthermore, this non-enclosing fitted shell arrangement prevents wrinkling, folding, or bunching together of the baffle material within the implant. Additionally, the outer shell is supported, feels smooth externally, and does not fold upon itself.

The architecture of the implant consists of a series of shells with interacting surfaces that are in an aqueous fluid environment. Beginning with the interior surface of the outer shell, and progressing to the exterior surface of the inner shell, there will be a total of two interacting surfaces when one non-enclosing fitted shell is present, three interacting surfaces when two non-enclosing fitted shells are present, four interacting surfaces when three non-enclosing fitted shells are present, and so forth.

According to the present invention, the surface of at least one of the interacting shells is textured to provide a low coefficient of friction, preferably less than 2, as measured by a standard method such as ASTM D1894, and high slidability over an adjacent shell in an aqueous fluid environment, without the need for addition of a lubricating agent. This prevents intermittent sticking and friction between the interacting shells in an aqueous fluid environment without the need for addition of a lubricating agent, thereby providing the desirable tactile feel of the implant that is similar to natural breast tissue. Only one of the surfaces in each interacting surface pair needs to be textured to benefit from this invention, although it is contemplated that both surfaces in each interacting surface pair could be textured.

These and other advantages of the present invention will be understood from the description of the desirable embodiments, taken with the accompanying drawings.

DESCRIPTION OF THE PREFERRED EMBODIMENTS

Figure 1:
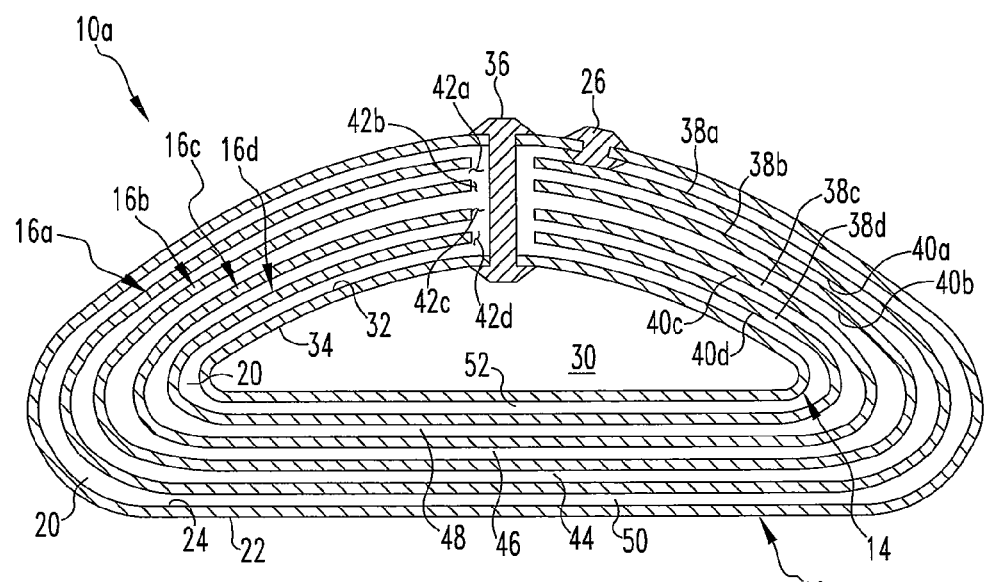
FIG. 1 is a cross-sectional side view of an implant, in accordance with the present invention.
Figure 2:
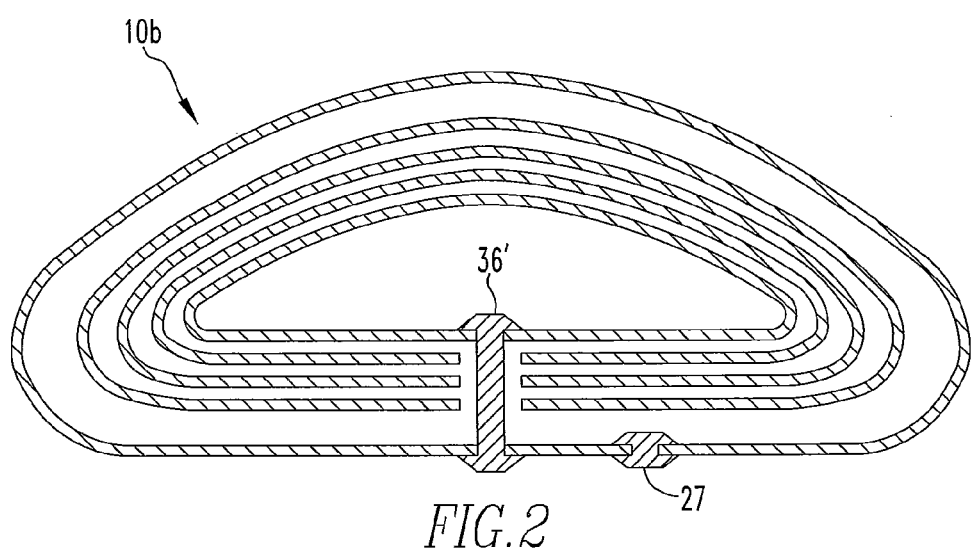
FIG. 2 is a cross-sectional side view of an implant according to an alternative embodiment.

Referring to FIGS. 1 and 2, implants 10a and 10b are particularly adapted for use as a surgically-implantable mammary prosthesis. The implant 10a of FIG. 1 includes an outer shell 12 enclosing a lumen or a compartment, an inner shell 14 enclosing a lumen or a compartment, and one or more generally dome-shaped non-enclosing fitted shells, e.g., a first non-enclosing fitted shell 16a, a second non-enclosing fitted shell 16b, a third non-enclosing fitted shell 16c and a fourth non-enclosing fitted shell 16d. The inner shell 14 and outer shell 12 are typically sealed with silicone "patches" by means known to those skilled in the art. In a particularly desirable embodiment, with reference to the implant 10a as it is oriented in the drawing, the dimensions of the outer shell 12 and the inner shell 14 are defined by a diameter measurement and a projection measurement. The diameter measurement is representative of the width of the implant 10a at its widest point and the projection measurement is representative of the height of the implant 10a at its tallest point. In this desirable embodiment, the diameter measurement of the implant 10a is greater than the projection measurement of the implant 10a. Thus, the implant 10a is substantially oval-shaped, elliptical-shaped, or parabolic-shaped. The first alternative embodiment implant 10b of FIG. 2 is similar in form and function as the implant 10a, except for the differences explicitly discussed herein.

With reference to FIG. 1, the outer shell 12 defines an outer lumen 20 and includes an exterior surface 22 and an interior surface 24. The outer shell 12 may include a valve 26 that bridges a portion between the exterior surface 22 and the interior surface 24 of the outer shell 12. The valve 26 may be placed along various areas of the outer shell 12. (As shown in FIG. 2 the valve 27 is in the posterior portion of the outer shell 12.) The valves 26 and 27 allow for filling of the outer lumen 20 of the outer shell 12 with a fluid after the manufacture of the implant 10a, either before or after implantation into a patient. The fluid is preferably a saline solution, yet it is to be understood that the term fluid may refer to other aqueous solutions. The valve 26 also allows for the controlled removal of the fluid without damaging or destroying the implant 10a. Alternatively, the outer lumen 20 may be manufactured as a pre-filled and completely sealed member (not shown), and therefore, not require a valve 26 for the outer lumen 20.

The outer shell 12 is preferably constructed of a non-porous, flexible, biocompatible material, such as silicone elastomer. One preferred silicone is MED-6605, an acetoxy cure RTV silicone manufactured by NuSil Technology, LLC. Any other silicone from which non-porous shells can be molded is also contemplated by this invention. It is understood by those skilled in the art and by this invention that a reference to silicone includes, but is not limited to, the following classifications of silicones: RTV, HTV, liquid silicone rubbers, 1-part, 2-part, acetoxy cure, alkoxy cure, oxime cure, peroxide cure, moderate and high temperature cure, platinum-catalyzed cure, and tin-catalyzed cure. Other elastomeric materials contemplated by this invention include, but are not limited to, silicone co-polymers and biocompatible elastomers from which non-porous shells can be molded. The outer shell 12 has a wall of sufficient thickness to provide structural integrity to retain fluids while achieving the desired flexibility and malleability of the implant 10a. The outer shell 12 is substantially oval-shaped, with the top of the implant 10a having a convex shape, as oriented in the drawing. Thus, the shape of the implant 10a is defined by the overall external shape of the outer shell 12. In an exemplary embodiment, the enclosed volume within the outer shell 12 is 575 cc. Therefore, the outer shell 12 may accommodate say 575 cc of volume-displacing material, e.g., fluid, inner shell and non-enclosing fitted shells. It is to be understood that various other volumes of shells 12 may be utilized. According to a preferred embodiment of this invention a textured interior surface 24 of outer shell 12 is provided.

The inner shell 14 defines an inner lumen 30, and includes an exterior surface 32 and an interior surface 34. The inner shell 14 is smaller than the outer shell 12 in that the diameter measurement and/or the projection measurement are less than that of the implant 10a. The inner shell 14 is also substantially oval-shaped. In an exemplary embodiment, the enclosed volume of the inner shell 14 is 345 cc. The inner shell 14 is situated within the outer lumen 20 of the outer shell 12, in a relatively central position with respect to interior surface 24 of the outer lumen 20. Similar to the outer shell 12, the inner shell 14 may include a valve 36. The valve 36 bridges the exterior surface 32 and the interior surface 34 of the inner shell 14, as well as the exterior surface 22 and the interior surface 24 of the outer shell 12, or the valve bridges a patch (not shown) that seals the inner shell and outer shell. The valve 36 allows for filling of the inner lumen 30 of the inner shell 14 with the fluid after the manufacture of the implant 10a, either before or after implantation into a patient. The valve 36 also allows for the controlled removal of fluid without damaging or destroying the implant 10a. The inner shell 14 is preferably constructed of a non-porous, flexible, biocompatible material, such as silicone elastomer. One preferred silicone is MED-6605, an acetoxy cure RTV silicone manufactured by NuSil Technology, LLC. In addition to this elastomer, materials contemplated by this invention include, but are not limited to, any other silicone, silicone co-polymers and biocompatible elastomers from which non-porous shells can be molded.

Referring to FIG. 1, once implanted, the top of the implant 10a faces away from the chest wall of a patient. Thus, if the implant 10a is not pre-filled, it is desirable to have the valve 26 for the outer lumen 20 situated at the top of the implant 10a and valve 36 for the inner lumen 30 situated at the back of the implant. This allows the implant 10a to be easily filled after it has been implanted in the patient. The valves 26, 36 may be situated along other areas of the exterior surface 22 of the outer shell 12 or the patch.

One or more non-enclosing fitted shells are situated within the outer lumen 20 of the outer shell 12. It is to be appreciated that there exists an optimal number of non-enclosing fitted shells for effectively achieving the objects of the present invention. The optimal number of shells is based upon the characteristics of the implant, e.g., the needs of the patient, the dimensions of the implant, the type of fluid used, etc. Each non-enclosing fitted shell is preferably constructed of a porous or non-porous, flexible, biocompatible material, such as silicone elastomer, having similar construction in shape as that of the inner shell 14 or the outer shell 12. One preferred silicone is MED-6605, an acetoxy cure RTV silicone manufactured by NuSil Technology, LLC. In addition to this elastomer, materials contemplated by this invention include, but are not limited to, any other silicone, silicone co-polymers and biocompatible elastomers from which porous or non-porous shells can be molded. It is to be understood that the non-enclosing fitted shells may be of varying thicknesses in different areas, relative to each other and relative to the inner shell 14 and the outer shell 12. Desirably, the non-enclosing fitted shells are to be as thin as possible, so as to minimize any bulk within the implant 10*a*. Furthermore, the non-enclosing fitted shells may either be porous or non-porous. Examples of porosity introduced in a non-enclosing fitted shell include, but are not limited to, features such as holes, slits, flaps, and any other openings in the non-enclosing fitted shell that allow the free flow of fluid between volumes on either side of the non-enclosing fitted shell. One preferred embodiment of this invention is to provide a textured interior surface on the non-enclosing fitted shells in an assembled breast prosthesis.

In the embodiment of FIG. 1 the implant 10*a* includes four non-enclosing fitted shells, and in the embodiment of FIG. 2 the implant 10*b* include only three non-enclosing fitted shells: the first non-enclosing fitted shell 16*a*, the second non-enclosing fitted shell 16*b*, the third non-enclosing fitted shell 16*c*, (and the fourth non-enclosing fitted shell 16*d* in the case of implant 10*a*), although it is to be understood that any number of non-enclosing fitted shells may be utilized. Each non-enclosing fitted shell 16*a*-16*d* includes an exterior surface 38*a*-38*d* and an interior surface 40*a*-40*d*, respectively. Each non-enclosing fitted shell 16*a*-16*d* may have a portion perforated and/or incised as in the case of implant 10*a*, thereby forming non-enclosing fitted shell openings 42*a*-42*d* in non-enclosing fitted shells 16*a*-16*d*, respectively, that allows space for passage of a valve from the outer shell 12 to the inner shell 14 and/or for a patch connecting the outer shell 12 to the inner shell 14. The dimensions of each non-enclosing fitted shell are also defined by a diameter measurement and a projection measurement. The diameter measurement is representative of the length of the non-enclosing fitted shell at its widest point and the projection measurement is representative of the height of the non-enclosing fitted shell at its tallest point.

If more than one non-enclosing fitted shell is utilized, as depicted in FIG. 1, then the non-enclosing fitted shells 16*a*-16*d* are contained within each other. Thus, it is preferable that the sizes of the non-enclosing fitted shells 16*a*-16*d* be graduated, in that either the diameter measurement, the projection measurement, or both the diameter and projection measurements of each non-enclosing fitted shell are incrementally larger or smaller than the preceding or successive non-enclosing fitted shells, respectively. For example, in an exemplary embodiment, the unenclosed volume measurements of the non-enclosing fitted shells 16*a*-16*d* are 555 cc, 515 cc, 475 cc, and 440 cc, respectively, with the non-enclosing fitted shells 16*a*-16*d* spaced between 0 cm and 1.0 cm apart from each other. The resultant graduated arrangement occupies the outer lumen 20 of the outer shell 12 with the inner shell 14 enveloped by the non-enclosing fitted shells 16*a*-16*d*. It is to be understood that some of the non-enclosing fitted shells 16*a*-16*d* may be the same size as each other and therefore, not necessarily embody a graduated arrangement. The non-enclosing fitted shell openings 42*a*-42*d* are sized such that the inner shell 14 does not fit through the non-enclosing fitted shell openings 42*a*-42*d*. Thus, the fourth non-enclosing fitted shell 16*d*, having the smallest volume measurement, is adjacent to the exterior surface 32 of the inner shell 14 and the first non-enclosing fitted shell 16*a*, having the largest volume measurement, is adjacent to the interior surface 24 of the outer shell 12. The second non-enclosing fitted shell 16*b* and the third non-enclosing fitted shell 16*c* are situated between the first non-enclosing fitted shell 16*a* and the fourth non-enclosing fitted shell 16*d* according to their volume measurements. Specifically, the second non-enclosing fitted shell 16*b* is adjacent to the first non-enclosing fitted shell 16*a* and the third non-enclosing fitted shell 16*c* is adjacent to the fourth non-enclosing fitted shell 16*d*. This graduated arrangement creates a space between each of the non-enclosing fitted shells and a space between both the inner and outer shells and the non-enclosing fitted shells. Thus, a space 44 is between the first non-enclosing fitted shell 16*a* and the second non-enclosing fitted shell 16*b*, a space 46 is between the second non-enclosing fitted shell 16*b* and the third non-enclosing fitted shell 16*c*, and a space 48 is between the third non-enclosing fitted shell 16*c* and the fourth non-enclosing fitted shell 16*d*. Similarly, a space 50 is between the outer shell 12 and the first non-enclosing fitted shell 16*a* and a space 52 is between the inner shell 14 and the fourth non-enclosing fitted shell 16*d*.

Beginning with the exterior surface of the outer shell, and progressing to the interior surface of the inner shell, there will be a total of two interacting surfaces when one non-enclosing fitted shell is present, three interacting surfaces when two non-enclosing fitted shells are present, four interacting surfaces when three non-enclosing fitted shells are present, and so forth. At least one of the surfaces in each interacting surface pair needs to be physically textured to provide a low coefficient of friction and high slidability between the pair of shells in an aqueous fluid environment without the addition of a lubricating agent. Hence, according to one embodiment of the present invention a textured exterior surface is provided on the one or more non-enclosing fitted shells and a textured exterior surface is provided on the inner shell in an assembled breast prosthesis.

Insertion of the fluid into the outer lumen 20 of the outer shell 12 causes the fluid to fill the outer lumen 20 and to also envelop the non-enclosing fitted shells 16*a*-16*d* by flowing into the spaces 44, 46, 48, 50, and 52. The shape, size, and graduated arrangement of the non-enclosing fitted shells 16*a*-16*d* result in the non-enclosing fitted shells 16*a*-16*d* maintaining their relative positions within the outer shell 12 and prevent the non-enclosing fitted shells 16*a*-16*d* from wrinkling, folding, or bunching together, which would otherwise be felt as a bulge through the outer shell 12. In conjunction with the inner shell 14 filled with the fluid, this combination provides the implant 10*a* with the simulated static and kinetic (or dynamic) characteristics of natural breast tissue by supporting the outer shell to maintain volume in an area and by reducing the displacement rate of fluid from an area when the implant is manipulated or when the patient changes position. Furthermore, sloshing, "fluid waves" and bouncing are reduced or prevented. Consequently, a breast reconstructed or enhanced with either the implant 10*a* or the alternative embodiments implants will feel like a natural breast and will approximate the movement and feel of the natural breast.

The textured shell surfaces of an assembled breast prosthesis contemplated by the present invention include a texture on one of the surfaces for each of the interacting surface pair of an assembled breast prosthesis. The interacting surface combinations contemplated by this invention include (1) a textured interior surface of the outer shell and textured interior surfaces of the non-enclosing fitted shells, and (2) textured exterior surfaces of the non-enclosing fitted shells and a textured exterior surface of the inner shell. A suitable method of applying this texture to the shells is to alter the surface of the mandrel (or "mold") used to form the shells with impact, or abrasive, media. These surface texture features can be contiguous over the surface of the mandrel or discrete islands or other patterns distributed over the mandrel surface. The mandrel, or mold, surface texture is then imprinted into the interior surface of the silicone shell when removed from the mold. To achieve a final assembled configuration of at least one textured surface in each of the interacting surface pairs, the interior surface of the inner shell, non-enclosing fitted shells, or outer shell can be textured and any particular shell could be inverted prior to assembly to cause the textured surface to be the exterior surface of the particular shell after assembly.

Impact media is used in a variety of industries to perform functions such as deburring surfaces, and preparing surfaces for coating or painting. The choice of impact media and means of contacting the impact media to the surface of an article depend on the article material, geometry, and size. There are also impact media grit size ranges available and used in these industries. There are numerous types of impact media including, but not limited to, silica, alumina, garnet, glass beads, metal particles, nutshells, pumice, silicon carbide, plastics/polymers, zirconia, and other ceramics.

The impact media is forced to contact the surface of an article such as a mold, thereby altering the surface characteristics (e.g., the height and/or depth of the texture features, separation distance between texture features, and smoothness of the texture features). Surface roughness is the measure of the surface irregularities in a surface texture. The irregularities are the result of the manufacturing processes and post-processing (i.e., finishing) employed to create the surface. Surface roughness Ra is defined as the arithmetic average deviation of the surface valleys and peaks typically expressed in the units of micro inches or micro meters ("microns").

One currently preferred embodiment is to use an impact medium particle having the morphological features of an irregular shape and/or a non-smooth surface to texture the mold surface. Preferred impact media having an irregular shape and/or non-smooth surface include, but are not limited to, aluminum oxide ("alumina"), silica, silicon carbide, pumice, zirconia, and other ceramics. The preferred mold surface is a polymer, including, but not limited to polyoxymethylene, polytetrafluoroethylene, polyethyelene, polydimethylsiloxane, polyamides, and polyethylene terephthalate, although other surfaces such as aluminum, titanium or stainless steel are contemplated. It is also contemplated that a mold surface could be a polymer coating on metals such as stainless steel, aluminum, and titanium.

Figure 3:
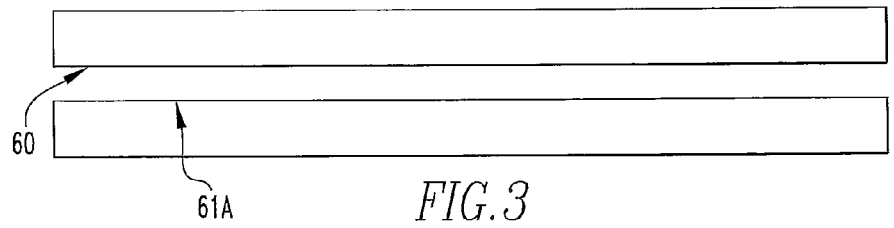
FIG. 3 is a schematic illustration of two adjacent surfaces for explaining sliding contact not according to this invention.
Figure 4:
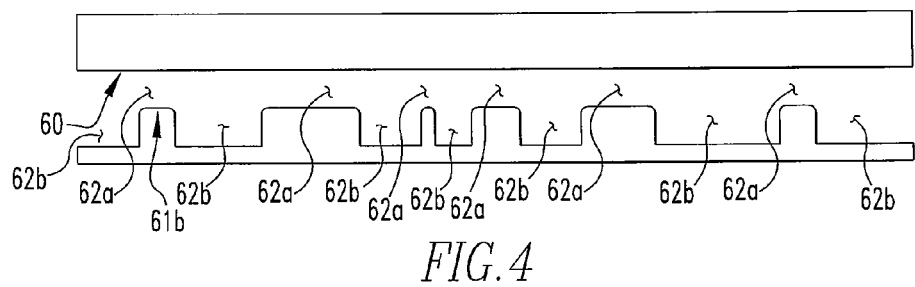
FIGS. 4 and 5 are schematic illustrations of two adjacent surfaces one of which is textured for explaining sliding contact according to this invention.
Figure 5:
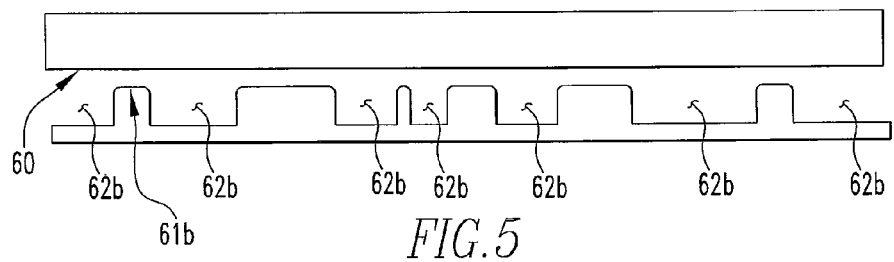

Referring to FIGS. 3, 4, and 5, friction, or sticking, of two surfaces results from chemical interaction of surface species or physical interaction of interlocking asperities on the surfaces. How two surfaces interact and slide across each other is dependent on the contact area between the two surfaces, the chemical or physical properties of the surfaces, and the amount or volume of aqueous fluid between the surfaces that can act as a lubricant. According to this invention, decreasing the contact area for interaction of the surface chemical species is one means to reduce the degree of chemical interaction and increase slidability between surfaces. Another means is decreasing the contact area for interaction of the surface physical properties, such as by changing the number, shape and/or size of the surface features, to reduce the degree of physical interaction and coefficient of friction and increase slidability between surfaces; however, a texture on interacting surfaces may not always be beneficial since interlocking and increased friction can occur depending on the shape, height and/or depth of the texture features, separation distance between texture features, and smoothness of the texture features. Maintaining a sufficient amount or volume of fluid between interacting surfaces so it can act as a lubricant, such as by use of a texture on at least one of the interacting surfaces to keep sufficient fluid at the surface in reservoirs, is another means to decrease the coefficient of friction and increase slidability between surfaces. A sufficient amount or volume of fluid in reservoirs between two interacting surfaces is depicted by the areas 62b in FIGS. 4 and 5. The sufficient amount or volume of fluid in areas 62b kept at the surface in reservoirs to act as a lubricant provides for a low coefficient of friction and high slidability between the interacting surfaces, without the addition of any lubricating agents to the fluid.

The shells are nested in the breast implant so that the texture transferred to the interior silicone surface by the mold surface is in contact with a relatively smooth exterior silicone surface as depicted in FIGS. 4 and 5. For a polyoxymethylene (e.g., Delrin®) or polytetrafluoroethylene (e.g., Teflon®) mold, the preferred grit size range for the alumina impact media is about 100 to 500, and more preferably between about 200 to 400. One preferred embodiment for the surface roughness Ra on a polyoxymethylene or polytetrafluoroethylene mold that forms the RTV silicone shells is about 30-150 micro inch, and more preferably about 50-100 micro inch. The optimal surface roughness to maintain a sufficient amount or volume of fluid between interacting surfaces to act as a lubricant to provide a low coefficient of friction and high slidability will depend on the mold material, grit size and grit material used to texture the mold, the specific elastomeric material formed on the mold, the thickness of the elastomeric shell, and the surface chemistry of the elastomeric material.

A textured surface that interacts with a smoother surface can reduce the coefficient of friction between the two surfaces. In FIG. 3, a smooth silicone surface 60 is brought into contact with a smooth silicone surface 61a. The entire surface of 61a can interact with the surface 60. Whereas, as in the case of FIGS. 4 and 5, only parts of the areas depicted by surface 61b can interact with surface 60. The total surface area for interaction for surfaces 60-61b is reduced compared to 60-61a. The areas 62b also provide reservoirs to maintain a sufficient amount or volume of fluid (e.g., saline) between interacting surfaces to act as a lubricant to provide a low coefficient of friction and high slidability between the surfaces when brought into contact in an aqueous fluid environment. Depending on the relative size and geometries of the textured surface features, a higher or lower coefficient of friction between the textured surface and the smooth surface may result. Therefore, the characteristics of the surface features on each of the interacting surfaces is important and must be appreciated to provide the desired low coefficient of friction and high slidability of interacting surfaces. Those skilled in the art will understand that the static and kinetic coefficient of friction can be measured using a standard such as ASTM D1894, "Standard Test Method for Static and Kinetic Coefficients of Friction of Plastic Film and Sheeting". This method can be adapted for measurements in an aqueous environment. The static coefficient of friction $\mu_s$ is defined by $F_s \leq \mu_s F_n$, where $F_s$ is the frictional force between two surfaces tangential to the surface contact plane, and $F_n$ is the normal (or perpendicular) force between the two surfaces. The kinetic (or dynamic) coefficient of friction $\mu_k$ is defined by $F_k = \mu_k F_n$, where $F_k$ is the force required to maintain a tangential motion of the two surfaces across each other. Measurements using a standard such as this can then be used to select the surface texture for a given mold material that produces shells with a low coefficient of friction and high slidability between them, thereby providing the means for producing tactile properties of the surgically-implantable prosthetic device that are similar to natural breast tissue. For example, both the static and kinetic coefficients of friction between two silicone surfaces in an aqueous fluid environment were measured based on ASTM D1894. For various interacting silicone shell surface combinations (e.g., smooth-to-smooth, textured-to-textured, smooth-to-textured) the measured static and kinetic coefficients of friction ranged between about 1 and 5. The static coefficient of friction between two or more interacting shells in an aqueous fluid environment that produces the desired natural feel of the implant similar to natural breast tissue, is preferably less than about 2, and the preferred kinetic coefficient of friction is less than about 2. More preferably, the static and kinetic coefficients of friction in an aqueous fluid environment are both less than about 1.5.

In addition to a surface that is textured, another surface contemplated by the present invention to provide a low coefficient of friction and high slidability may be a coating applied on at least one of the surfaces of an interacting surface pair of an assembled breast prosthesis. Suitable coatings that chemically or mechanically bond to a surface include MED-6670 sold by NuSil Technology LLC and Slick Sil LSR sold by Solutions Group, LLC. The coating must, of course, be non-toxic and approvable by the authorities having jurisdiction over implantable prostheses. These surface modifications can be contiguous over the surface of the shell or discrete islands distributed over the shell surface. To achieve at least one coated surface in each of the interacting surface pairs comprising the implant, a shell may have one surface coated and then the shell can be inverted.

Another surface contemplated by the present invention to provide a low coefficient of friction and high slidability may be a chemical modification of at least one of the surfaces of an interacting surface pair of an assembled breast prosthesis. For example, a shell surface can be exposed to a plasma beam comprised of inert gases, such as helium or nitrogen, or reactive gases, such as oxygen, or excimer radiation. Plasma treatment or excimer irradiation of a silicone surface can create functional surface entities with improved wet-ability and/or lower friction properties than the underlying silicone. The plasma or irradiation created surface entities can also be further reacted with chemicals to change the chemical and physical properties of the surface. To achieve at least one chemically modified surface in each of the interacting surface pairs comprising the implant, a shell may have one surface chemically modified and then the shell can be inverted.

Another surface contemplated by the present invention to provide a low coefficient of friction and high slidability may be a physical modification of at least one of the surfaces of an interacting surface pair of an assembled breast prosthesis by spraying the shell material or by imprinting the shell material before it is cured with a separate material that is textured.

Having thus described our invention with the detail and particularity required by the Patent Laws, what is desired protected by Letters Patent is set forth in the following claims.

The invention claimed is:

1. A surgically-implantable prosthetic device comprising:
an outer shell having an exterior surface, an interior surface, and enclosing a lumen, wherein the lumen enclosed by the outer shell is able to accommodate a first fluid therein;
an inner shell having an exterior surface, an interior surface, and enclosing a lumen, wherein the lumen enclosed by the inner shell is able to accommodate a second fluid therein;
non-enclosing fitted shells situated between the exterior surface of the inner shell and the interior surface of the outer shell such that all surfaces of the non-enclosing fitted shells are in communication with the first fluid, said non-enclosing fitted shells defining at least two interacting shell surface pairs; and
at least one shell surface in the at least one interacting shell surface pair being textured to reduce the coefficient of static friction value to less than about 2 between the interacting shell surfaces.

2. The prosthetic device according to claim 1, whereby the outer shell, inner shell, and the one or more non-enclosing fitted shells are constructed of a material selected from the group consisting of silicones, silicone co-polymers or biocompatible elastomers.

3. The prosthetic device according to claim 1, whereby the outer shell, inner shell, and the one or more non-enclosing fitted shells are all of an RTV silicone.

4. The prosthetic device according to claim 1, wherein the first fluid and second fluid are substantially aqueous.

5. The prosthetic device according to claim 1, wherein the coefficient of friction is the kinetic coefficient of friction having a value less than about 2.

6. The prosthetic device according to claim 1, wherein the surface texture of the at least one shell surface in the at least one interacting shell surface pair is selected from the group consisting of contiguous over the surface of said shell, comprised of discrete islands distributed over the surface of said shell, and patterns distributed over the surface of said shell.

7. The prosthetic device according to claim 1, wherein the one or more non-enclosing fitted shells comprise an innermost non-enclosing fitted shell and an outermost non-enclosing fitted shell, wherein the innermost non-enclosing fitted shell is adjacent to the exterior surface of the inner shell and the outermost non-enclosing fitted shell is adjacent to the interior surface of the outer shell.

8. The prosthetic device according to claim 1, wherein each non-enclosing fitted shell is generally dome-shaped and has a diameter measurement and a projection measurement, and the projection measurement increases as the diameter measurement increases.

9. The prosthetic device according to claim 1, wherein the diameter measurement of one of the non-enclosing fitted shells is greater than the diameter measurement of any other non-enclosing fitted shell.

10. The prosthetic device according to claim 1, wherein the non-enclosing fitted shells are arranged in a graduated manner based upon the diameter measurement of each non-enclosing fitted shell, wherein the non-enclosing fitted shell having the smallest diameter measurement is adjacent to the exterior surface of the inner shell and wherein the non-enclosing fitted shell having the largest diameter is adjacent to the interior surface of the outer shell.

11. The prosthetic device according to claim 1, wherein one or more non-enclosing fitted shells have one or more porosity features allowing the free flow of said first fluid between volumes on either side of said non-enclosing fitted shell.

12. The prosthetic device according to claim 1, whereby the surgically-implantable prosthetic device is a breast implant.

13. The prosthetic device according to claim 1, wherein the texture of the at least one shell surface in the at least one interacting shell surface pair is imprinted into the at least one shell surface by the texture of a mold.

14. The prosthetic device according to claim 1, wherein:
- the outer shell, inner shell and one or more non-enclosing fitted shells are comprised of a silicone elastomer;
- the first fluid and the second fluid are saline solutions;
- the texture on the at least one shell surface of the at least one interacting shell surface pair is imprinted onto the at least one shell surface by the surface texture of the mold whereby the mold surface is comprised of a material selected from the group consisting of polyoxymethylene and polytetrafluoroethylene;
- the surface texture of the mold is applied using aluminum oxide impact media having a grit size between about 100 and 500; and
- the surface texture of the mold has a surface roughness between about 30 and 150 micro inch;
- the static coefficient of friction between the interacting shells is less than about 2; and
- the kinetic coefficient of friction between the interacting shells is less than about 2.

* * * * *